US009603807B2

(12) United States Patent
Kellum et al.

(10) Patent No.: US 9,603,807 B2
(45) Date of Patent: *Mar. 28, 2017

(54) ENTERAL ADMINISTRATION OF SORBENT POLYMER FOR TREATMENT AND PROPHYLAXIS OF INFLAMMATION

(71) Applicant: University of Pittsburgh—Of the commonwealth System of Higher Education, Pittsburgh, PA (US)

(72) Inventors: John A. Kellum, Pittsburgh, PA (US); Mitchell P. Fink, Los Angeles, CA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/025,322

(22) Filed: Sep. 12, 2013

(65) Prior Publication Data

US 2014/0017309 A1    Jan. 16, 2014

Related U.S. Application Data

(63) Continuation of application No. 13/122,223, filed as application No. PCT/US2009/059426 on Oct. 2, 2009, now Pat. No. 8,647,666.

(60) Provisional application No. 61/102,052, filed on Oct. 2, 2008.

(51) Int. Cl.
| | | |
|---|---|---|
| *A61K 9/50* | (2006.01) | |
| *A61K 31/75* | (2006.01) | |
| *A61K 31/79* | (2006.01) | |
| *A61K 31/745* | (2006.01) | |
| *A61K 9/20* | (2006.01) | |
| *A61K 9/00* | (2006.01) | |

(52) U.S. Cl.
CPC .......... *A61K 9/5026* (2013.01); *A61K 9/0031* (2013.01); *A61K 9/0065* (2013.01); *A61K 9/2081* (2013.01); *A61K 31/745* (2013.01); *A61K 31/75* (2013.01); *A61K 31/79* (2013.01)

(58) Field of Classification Search
CPC ...... A61K 31/75; A61K 31/79; A61K 31/745; A61K 9/0031; A61K 9/0065; A61K 9/2081; A61K 9/5026; A61K 2300/00
USPC .... 424/464, 497, 78.32, 451, 469, 474, 475, 424/483, 484, 489, 490, 501
See application file for complete search history.

(56) References Cited

U.S. PATENT DOCUMENTS

| | | | | |
|---|---|---|---|---|
| 4,172,120 A | * | 10/1979 | Todd ................... | A61K 9/0007 424/43 |
| 4,404,346 A | * | 9/1983 | Pirotta et al. ................... | 521/29 |
| 4,510,128 A | * | 4/1985 | Khanna ....................... | 424/78.16 |
| 5,112,758 A | * | 5/1992 | Fellman et al. ................... | 436/8 |
| 8,647,666 B2 | * | 2/2014 | Kellum et al. ................. | 424/451 |
| 2002/0182168 A1 | * | 12/2002 | Holmes-Farley .... | A61K 31/785 424/78.08 |
| 2003/0054037 A1 | * | 3/2003 | Babcock et al. .............. | 424/486 |
| 2006/0280776 A1 | * | 12/2006 | Koide ........................... | 424/439 |
| 2008/0138434 A1 | * | 6/2008 | Brady et al. ................... | 424/529 |
| 2011/0178002 A1 | * | 7/2011 | Dieckgraefe ...... | A61K 31/7008 514/2.9 |
| 2012/0040025 A9 | * | 2/2012 | Currie ................ | A61K 31/4706 424/725 |
| 2014/0112980 A1 | * | 4/2014 | Vaghefi ................ | A61K 9/1617 424/452 |

FOREIGN PATENT DOCUMENTS

| | | |
|---|---|---|
| EP | 1 245 238 A2 | 10/2002 |
| WO | WO 94/13697 A1 | 6/1994 |
| WO | WO 94/26921 A1 | 11/1994 |
| WO | WO 03/009885 A2 | 2/2003 |
| WO | WO 2008/021970 A2 | 2/2008 |

OTHER PUBLICATIONS

Watanabe et al. ("Efficacy of bacteriophage therapy against gut-delivered sepsis caused by Pseudomonas aeruginosa in mice" in Antimicrobial Agents and Chemotherapy, Feb. 2007, p. 446-252).*
European Patent Office, Supplementary European Search Report in EP 09818588.7 (Mar. 14, 2013).
Fink et al., "Epithelial Barrier Dysfunction: A Unifying Theme to Explain the Pathogenesis of Multiple Organ Dysfunction at the Cellular Level," *Critical Care Clinics*, 21(2): 177-196 (Apr. 2005).
Hoyt et al., "Working Group on Trauma Research Program Summary Report," *The Journal of Trauma*, 57(2): 410-415 (Aug. 2004).
International Preliminary Report on Patentability dated Apr. 14, 2011 in connection with PCT/US2009/059426.
International Search Report dated Dec. 4, 2009 in connection with PCT/US2009/059426.
Jackson et al., "Bile Mediates Intestinal Pathology in Endotoxemia in Rats," *Infection and Immunity*, 68(8): 4714-4719 (Aug. 2000).
Kellum et al., "Effect of hemofiltration filter adsorption on circulating IL-6 levels in septic rats," *Critical Care*, 6(5): 429-433 (Oct. 2002).
Kellum et al., "Hemoadsorption removes tumor necrosis factor, interleukin-6, and interleukin-10, reduces nuclear factor-κB DNA binding, and improves short-term survival in lethal endotoxemia," *Critical Care Medicine*, 32(3): 801-805 (Mar. 2004).

(Continued)

*Primary Examiner* — Blessing M Fubara
(74) *Attorney, Agent, or Firm* — Leydig, Voit & Mayer, Ltd.

(57) ABSTRACT

The invention provides a method of ameliorating inflammation in a patient involving administering to the patient a therapeutically effective dose of composition including polystyrene divinyl benzene copolymer and a polyvinyl pyrrolidone polymer. More particularly, the method relates to using these polymers as an enteral sorbent preparation to remove inflammatory mediators, such as cytokines, from the intestinal lumen. The polymers can be in the form of a preparation of polystyrene divinyl benzene copolymer beads with a biocompatible polyvinyl pyrrolidone polymer coating.

47 Claims, 3 Drawing Sheets

(56) References Cited

OTHER PUBLICATIONS

Figure 1:
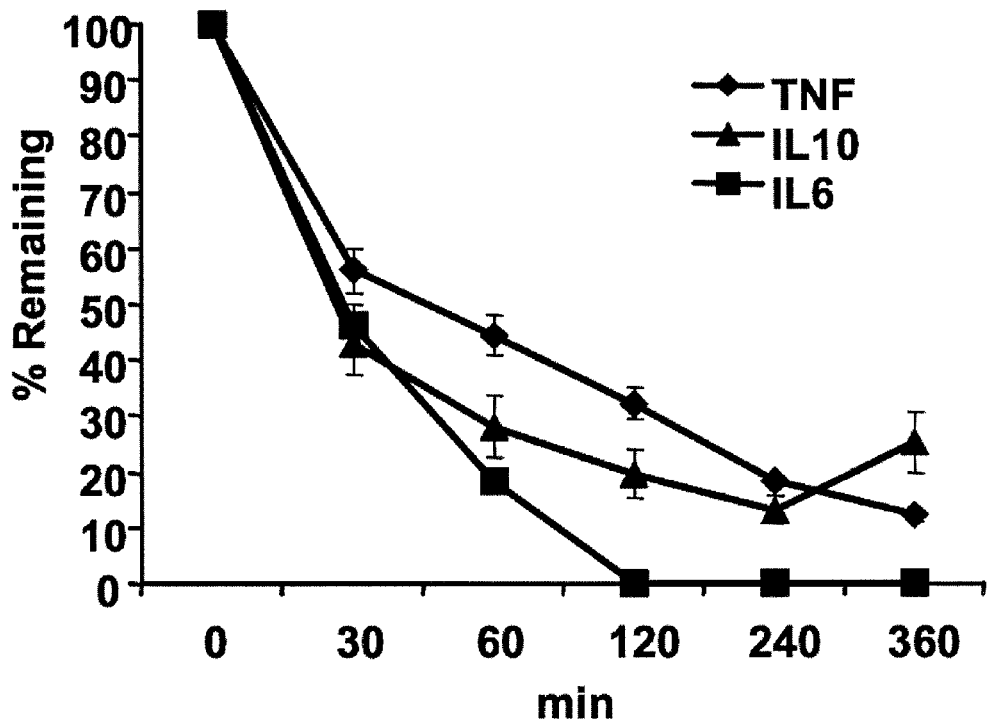

Macias et al., "Survival in a Rat Model of Lethal Hemorrhagic Shock is Prolonged Following Resuscitation with a Small Volume of a Solution Containing a Drag-Reducing Polymer Derived from Aloe Vera," *Shock*, 22(2): 151-156 (2004).
Peng et al., "Effects of hemoadsorption on cytokine removal and short-term survival in septic rats," *Critical Care Medicine*, 36(5): 1573-1577 (May 1, 2008).
Sims et al., "Ringer's ethyl pyruvate solution ameliorates ischemia/reperfusion-induced intestinal mucosal injury in rats," *Critical Care Medicine*, 29(8): 1513-1518 (Aug. 2001).
Song et al., "Cytokine Removal with a Novel Adsorbent Polymer," *Blood Purification*, 22: 428-434 (2004).
Thomson et al., "Role of Gastric Mucosal and Gastric Juice Cytokine Concentrations in Development of Bisphosphonate Damage to Gastric Mucosa," *Digestive Diseases and Sciences*, 48(2): 308-314 (Feb. 2003).
Tsuchida et al., "Blood Purification for Critical Illness: Cytokines Adsorption Therapy," *Therapeutic Apheresis and Dialysis*, 10(1): 25-31 (Feb. 2006).
Watanabe et al., "Efficacy of Bacteriophage Therapy against Gut-Derived Sepsis Caused by Pseudomonas aeruginosa in Mice," *Antimicrobial Agents and Chemotherapy*, 51(2): 446-452 (Feb. 2007).
Yao et al., "The inflammatory basis of trauma/shock-associated multiple organ failure," *Inflammation Research*, 47: 201-210 (1998).
Gardiner et al., "Adsorbents as antiendotoxin agents in experimental colitis," *Gut*, 34: 51-55 (1993).
Japanese Patent Office, Notice of Reasons for Refusal in JP 530276/2011 (Jan. 28, 2014).
Lv et al., "Hydroxyethyl Starch Exhibits Antiinflammatory Effects in the Intestines of Endotoxemic Rats," *Anesthesia & Analgesia*, 103(1): 149-155 (Jul. 2006).
Mexican Patent Office, Office Action in MX/a/2011/003569 (Dec. 18, 2013).
Sun et al., "Ketamine suppresses intestinal NF-kappa B activation and proinflamnnatory cytokine in endotoxic rats," *World Journal of Gastroenterology*, 10(7): 1028-1031 (2004).
Swank et al., "Role of the Gut in Multiple Organ Failure: Bacterial Translocation and Permeability Changes," World Journal of Surgery, 20: 411-417 (1996).
Australian Patent Office, Office Action in AU 2009298112 (Aug. 20, 2014).
Chinese Patent Office, Office Action in CN 200980148128.X (Jun. 12, 2013).
Chinese Patent Office, Office Action in CN 200980148128.X (Apr. 9, 2014).
Chinese Patent Office, Office Action in CN 200980148128.X (Oct. 11, 2014).
Mexican Patent Office, Office Action in MX/a/2011/003569 (Jun. 21, 2013).
Prosecution history of U.S. Appl. No. 13/122,223, filed May 17, 2011, current from Apr. 1, 2011 to Jan. 23, 2014.
Australian Patent Office, Office Action in AU 2009298112 (Sep. 2, 2015).
European Patent Office, Office Action in EP 09 818 588.7 (Apr. 19, 2016).
U.S. Appl. No. 13/122,223, filed May 17, 2011.
Canadian Patent Office, Notice of Allowance in CA 2,771,995 (Jun. 9, 2016).
Chinese Patent Office, Office Action in CN 200980148128.X (Jun. 1, 2016).
Barrett et al., *Anal. Chem.*, 73: 5232-5239 (2001).
Doi et al., *Int J. Mol. Sci.*, 12: 5213-5237 (2011).
Dressman et al., *Pharmaceutical Research*, 7(7): 756-761 (1990).
el Khoury et al., *Toxins*, 2: 461-493 (2010).
Huwig et al., *Toxicology Letters*, 122: 179-188 (2001).
Kim et al., *Encyclopedia of Surface and Colloid Science*, 4373-4381 (2002).
Madhyastha et al., *Fd Chem. Toxic*, 30(8): 709-714 (1992).
Peraica et al., *Arh Hig Rada Toksikol*, 53: 229-237 (2002).
Sales-Campos et al., *BioMed Research International*, 1-14 (2013).
Seeboth et al., *Veterinary Research*, 43(35): 1-11 (2012).
Sherrington, *Chem. Commun.*, 2275-2286 (1998).
Solfrizzo et al., *Mycopathologia*, 151: 147-153 (2000).
Supelco Product Specification "Amberlite XAD-2 Polymeric Adsorbent" (1997).
Canadian Intellectual Property Office, Office Action in Canadian Patent Application No. 2,771,995 (Aug. 25, 2015).
Chinese Patent Office, Office Action in CN 200980148128.X (Jun. 30, 2015).
Shuyun et al., *Clinical Pharmacology*, 2: 252 (1986).
Chinese Patent Office, Notice of Reexamination in Chinese Patent Application No. 200980148128.X (Dec. 1, 2016).

\* cited by examiner

ENTERAL ADMINISTRATION OF SORBENT POLYMER FOR TREATMENT AND PROPHYLAXIS OF INFLAMMATION

CROSS-REFERENCE TO RELATED APPLICATIONS

This application is a continuation of U.S. patent application Ser. No. 13/122,223, which is the U.S. national phase of PCT/US2009/059426, filed on Oct. 2, 2009, and which claims priority to U.S. Provisional Patent Application No. 61/102,052, filed Oct. 2, 2008, the contents of each of these prior applications are incorporated herein in their entirety.

FIELD OF THE INVENTION

Embodiments of the present invention relate to methods for the treatment of systemic inflammation. More particularly, embodiments of the present invention relate to a method of intralumenal adsorption of mediators of inflammation comprising administering to a patient a therapeutically effective dose of sorbent polymer.

BACKGROUND OF THE INVENTION

Generally, all forms of shock (e.g., hemorrhagic, cardiogenic, septic), tissue injury (e.g., surgery, injury to battlefield combatants), local gastrointestinal inflammatory disease (e.g., inflammatory bowel disease), and/or ischemia lead to activation of inflammatory mediators, coagulation factors, and oxidative stress. In particular the activation of various humoral (e.g., complement factors, coagulation factors) and cellular elements (neutrophils, endothelial cells, macrophages) results in the expression of numerous mediators (toxic oxygen species, proteolytic enzymes, adherence molecules, cytokines), which can produce generalized inflammation and further tissue injury, ultimately leading to multiple organ failure. Furthermore, injury to organs such as in the gut can result in loss of barrier function and propagation/amplification of the inflammatory response.

In 2004, the Working Group on Trauma Research Program Summary Report (Hoyt D B, Holcomb J, Abraham E., Atkins J, Sopko G, Working Group on Trauma Research: Working Group on Trauma Research Program summary report: National Heart Lung Blood Institute (NHLBI), National Institute of General Medical Sciences (NIGMS), and National Institute of Neurological Disorders and Stroke (NINDS) of the National Institutes of Health (NIH), and the Department of Defense (DOD), J Trauma 2004; 57: 410-5) concluded that the "ability to manipulate the immune response following injury is essential to improving postinjury therapy." However, systemic manipulation of the immune response can be risky given its inherent importance in fighting infection. Thus, a more targeted approach is likely to be potentially safer and more effective.

Potential targets include the plasma compartment and the gut lumen. There are at least four ways in which inflammatory mediators can be expressed in the gut lumen. First, inflammatory mediators can be produced systemically, absorbed by the liver and then delivered to the gut lumen via liver bile. Second, inflammatory mediators can be produced by the liver and then delivered to the gut lumen via liver bile. Third, gut epithelial cells can produce inflammatory mediators locally in the gut lumen. Finally, inflammatory mediators can be generated by bacteria in the gastrointestinal tract reacting with white blood cells.

The plasma compartment is an attractive target, since the local expression of inflammatory mediators in tissues can be protective whereas systemic release typically is not. Similarly, inflammatory toxins in the gut lumen injure cells and compromise barrier function without serving a beneficial host response. Whether produced by the liver or produced elsewhere and removed by the liver, inflammatory mediators, such as cytokines, are delivered to the small bowel via the bile where they can cause local injury and be readsorbed into the systemic circulation. Rats given lipopolysaccharide intravenously show improved survival when there was external drainage of bile resulting in some protection of the gastrointestinal tract.

SUMMARY

Embodiments of the present invention have been made in view of the above problems of the related art. One embodiment of the present invention provides a method of ameliorating systemic inflammation comprising initiating or exacerbating an inflammatory response in a patient and administering to the patient a therapeutically effective dose of a composition comprising a sorbent polymer, such as polystyrene divinyl benzene copolymer and a polyvinyl pyrrolidone polymer.

In accordance with an aspect of the invention, there is provided a method of mitigating the onset of shock comprising administering to the patient in need thereof a therapeutically effective dose of a sorbent polymer, such as polystyrene divinyl benzene copolymer and a polyvinyl pyrrolidone polymer.

Preferred embodiments of the present invention relate to polystyrene divinyl benzene copolymer and a polyvinyl pyrrolidone polymer. More particularly, embodiments of the present invention relate to using these polymers as an enteral sorbent preparation to remove inflammatory mediators, such as cytokines, from the intestinal lumen. Preferred embodiments of the present invention relate to a preparation of polystyrene divinyl benzene copolymer beads with a biocompatible polyvinyl pyrrolidone polymer coating.

BRIEF DESCRIPTION OF THE DRAWING FIGURES

The above and other features and advantages of embodiments of the present invention will become more apparent by describing in detail embodiments thereof with reference to the attached drawings.

FIG. 1 shows in vitro cytokine elimination. Data shown: means±SE for six pools of blood from two animals each. All time points were significantly different form time 0, $p<0.001$.

Figure 2:
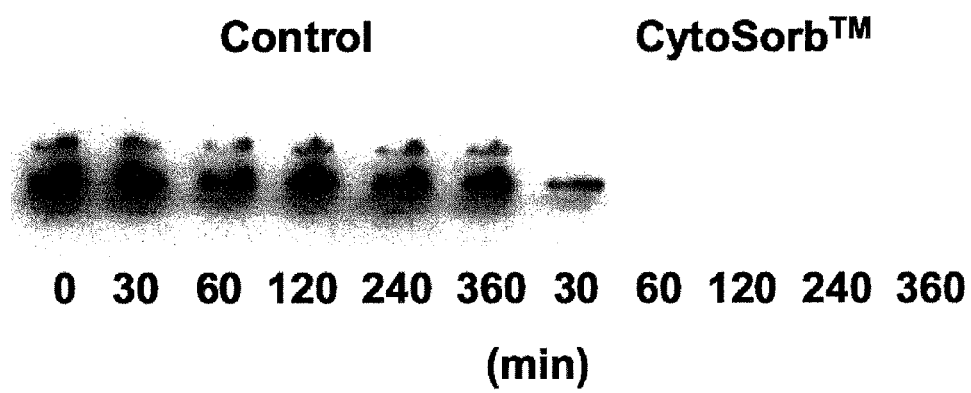

FIG. 2 shows immuoblots for HMBG-1 in RAW 264.7. Cells stimulated with LPS in the presence or absence of polymer.

Figure 3:
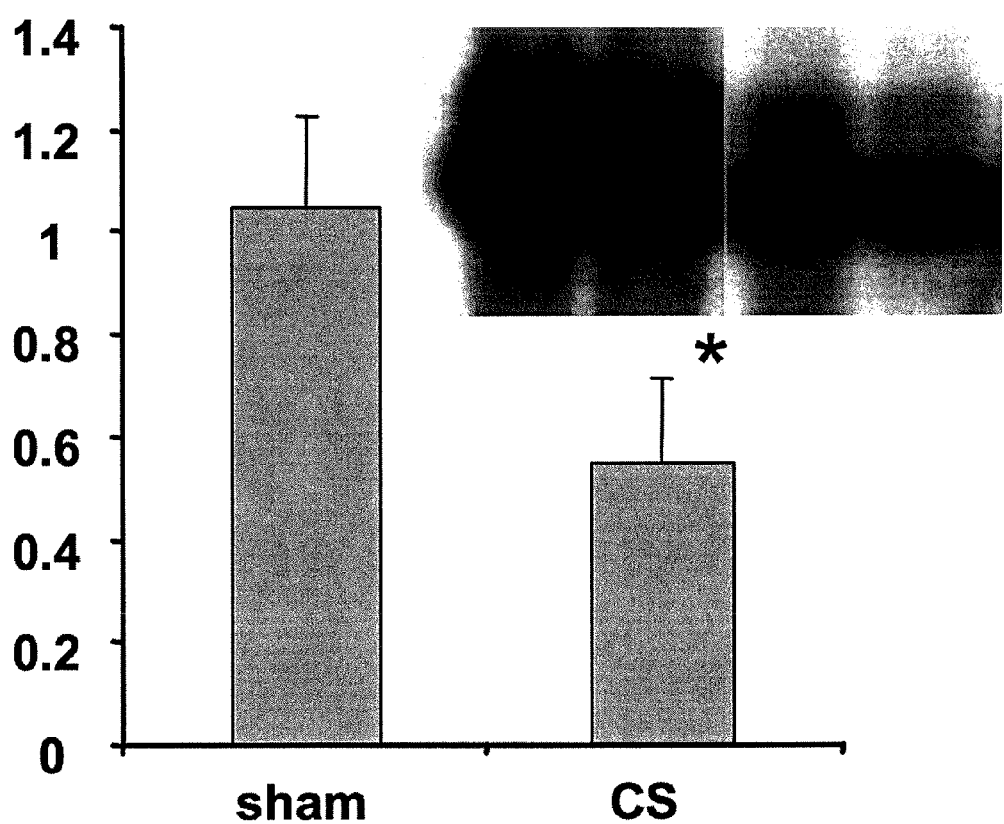

FIG. 3 shows $NF_{-k}B$ DNA-binding in livers of CYTOSORB vs. sham-treated animals at 4 h. Graph depicts mean data±SEM; $P<0.05$. Right panel depicts representative bands from the electrophoretic mobility shift assay. N=12 animals.

Figure 4:
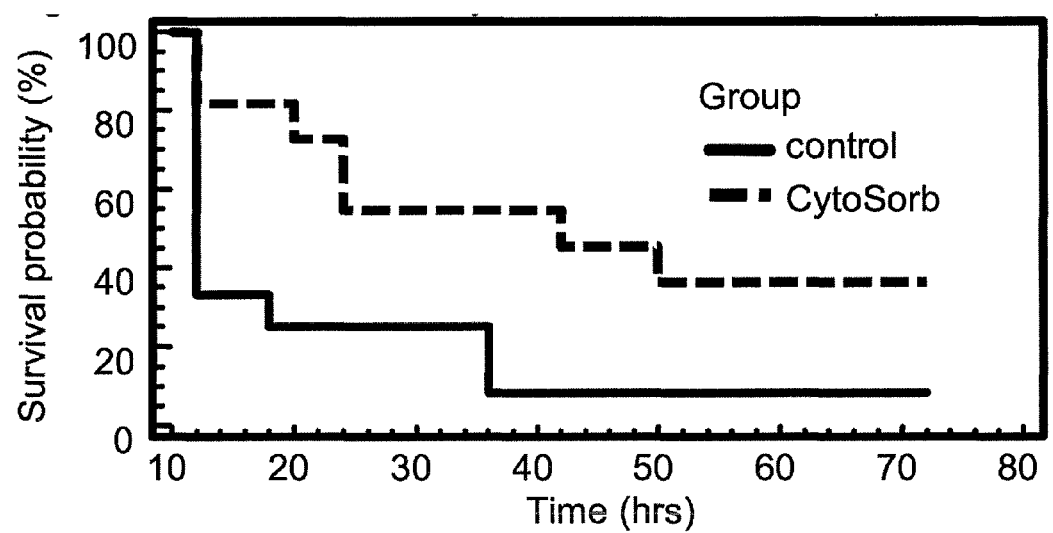

FIG. 4 shows the effect of enteral CYTOSORB on survival in septic rats.

DETAILED DESCRIPTION OF THE PREFERRED EMBODIMENTS

An embodiment of the present invention provides a method for the treatment of systemic inflammation. Also, embodiments of the present invention relate to a method of mitigating the effects of shock and/or to a method of intralumenal adsorption of mediators of inflammation.

In one embodiment, a therapeutically effective dose of a sorbent polymer is administered to a patient in need thereof. Sorbent polymers include polystyrene divinyl benzene copolymer and polyvinyl pyrrolidone polymer. A preferred composition comprises, consists essentially of, or consists of polystyrene divinyl benzene copolymer and polyvinyl pyrrolidone polymer.

In the context of the present invention, the patient is typically a human patient. However, the patent can alternatively be an animal patient (such as domestic animals (e.g., cattle, horses, sheep, goats, cats, dogs, etc.)), an animal used in laboratory research (such as mice, rats, and the like) or an animal of zoological interest (e.g., large cats, ungulates, elephants, etc.).

A composition of polystyrene divinyl benzene copolymer and polyvinyl pyrrolidone polymer can be in the form of beads. For purposes of this disclosure, the term "bead" refers to any solid three-dimensional particle. The bead shape can be spherical, spheroidal, ellipsoidal, ovoid, rod, or prismatic. As used herein, the term "diameter" in reference to beads refers to average diameter.

The beads can comprise polystyrene divinyl benzene copolymer, which can be further coated with polyvinyl pyrrolidone polymer. The beads can also consist essentially of, or consist of, polystyrene divinyl benzene copolymer and polyvinyl pyrrolidone polymer. The beads can be fabricated with pores on the outer surface. Molecules can enter the bead's interior via such pores. It is believed that inflammatory mediators are adsorbed within the pores as the beads adsorb the inflammatory mediators from the body of a patient. In one embodiment, the pores have a size of at least 10 Å, such as at least 20 Å, at least 30 Å, at least 40 Å, at least 50 Å, at least 60 Å, at least 70 Å, at least 80 Å or at least 90 Å (or at least about such values). The pores can have a size of as much as 100 Å, or as much as 90 Å, or as much as 80 Å, or as much as 70 Å, or as much as 60 Å, or as much as 50 Å, or as much as 40 Å, or as much as 30 Å, or as much as 20 Å (or as much as about such values). In one embodiment, the beads have a pore size of from 10 Å to 100 Å; in another, from 20 Å to 50 Å (or about such values). Beads can be fabricated to have specific pore sizes. The beads can thus be engineered to accommodate and target specific molecules of a particular size for removal. To capture multiple inflammatory mediators, the beads can have a variety of or distribution of pore sizes.

The beads can be of any suitable size and internal surface area. For example, beads can have a diameter of at least 200 µm, such as at least 300 µm, such as at least 400 µm, such as at least 500 µm, such as at least 600 µm, such as at least 700 µm (or at least about such values). The beads can have a diameter of up to 800 µm, such as up to 700 µm, such as up to 600 µm, such as up to 500 µm, such as up to 400 µm, such as up to 300 µm (or up to about such values). A non-limiting example of beads ranges from about 300 to about 800 microns in diameter. The internal surface area of the beads can be at least 700 m$^2$/gram of beads, such as at least 800 m$^2$/gram of beads, such as at least 900 m$^2$/gram of beads (or at least about such values). The internal surface area of the beads can be up to 1000 m$^2$/gram of beads, such as up to 900 m$^2$/gram of beads, such as up to 800 m$^2$/gram of beads (or up to about such values). A non-limiting example of beads has internal surface area of about 700 m$^2$/gram of beads to about 1000 m$^2$/gram of beads. In one embodiment, the composition comprises beads having internal surface area of about 850 m$^2$/gram of beads.

In another embodiment, the invention provides is a method of ameliorating systemic inflammation in a patient comprising identifying a patient suffering from or at risk of systemic inflammation; and administering to the patient a therapeutically effective dose of a composition comprising one or more sorbent polymers that adsorb mediators of inflammation. A preferred administration is via a feeding tube.

The mediators of inflammation can be associated with, for example, sepsis, shock (hemorrhagic, cardiogenic, septic), tissue injury (e.g., surgery, injury to battlefield combatants), ischemia and reperfusion, cytotoxic chemotherapy, chemotherapy using IL-2 or other cytokines, bone marrow manipulation, mesenteric hypoperfusion, gut-mucosal injury, local gastrointestinal inflammatory disease (e.g., inflammatory bowel disease), acute lung inflammation, pancreatitis, malaria or rheumatoid arthritis and other collagen vascular diseases. Thus, for example, the beads can adsorb cytokines. Non-limiting examples of inflammatory mediators that can be adsorbed include tumor necrosis factor (TNF), interleukin (IL)-6, IL-10, high mobility group protein (HMGB)-1, IL-8, IL-18, monocyte chemotactic protein (MCP)-1, IL-2, IL-1β, and S100B.

The beads can be administered, e.g., orally, in the form of a pill (e.g., capsules, tablets and the like). Such pills comprise the beads and, optionally, pharmaceutically acceptable excipients such as binders, fillers, buffers, and the like. Such excipients are well known in the art, and suitable excipients can be selected by one of ordinary skill in the art without undue experimentation. In another embodiment, the composition can be administered in the form of a slurry, gel, powder, or other form suitable for oral administration.

Embodiments of sorbent polymers, such as polystyrene divinyl benzene copolymer and polyvinyl pyrrolidone polymer, preferably in bead form, can be administered to a patient in need thereof to adsorb inflammatory mediators. The administration can be prophylactic (e.g., preceding the onset of inflammation), during, or after the cause of the release of the inflammatory mediators.

Administration according to embodiments of the present invention can be any suitable administration that allows a sorbent polymer to be found in the gastrointestinal tract. For example, the administration can be oral, rectal, via a feeding tube, or direct administration into the gastrointestinal tract. A preferred administration is oral or via a feeding tube, though other routes of administration can be used. An oral administration of embodiments of the present invention allows a sorbent polymer, such as a polystyrene divinyl benzene copolymer and polyvinyl pyrrolidone polymer, to pass normally through the gastrointestinal tract of most individuals. Such administration allows a sorbent polymer, such as polystyrene divinyl benzene copolymer and polyvinyl pyrrolidone polymer, to enterally adsorb inflammatory mediators.

The polystyrene divinyl benzene copolymer and polyvinyl pyrrolidone polymer can be in the form of beads, as discussed herein. Such beads can be orally administered in the form of a pill or a slurry. The pill can include the beads and other ingredients, such as fillers. The slurry can include the beads and other ingredients, such as a carrier liquid. A pill or slurry formulation can be prepared similar to an activated charcoal pill or slurry, substituting beads of the embodiments of the present invention for the activated charcoal.

A form of polystyrene divinyl benzene copolymer and polyvinyl pyrrolidone polymer beads is manufactured by RenalTech International LLC, now doing business as MedaSorb Technologies, Inc. (Princeton, N.J.). MedaSorb manufactures polystyrene divinyl benzene copolymer beads with a biocompatible polyvinyl pyrrolidone polymer coating under the tradenames of CYTOSORB and BETASORB. Both CYTOSORB and BETASORB beads are envisioned to fall within the scope of embodiments of the present invention. The CYTOSORB beads are approximately 300-800 μm in size and have pores of a size of approximately 20-50 Å.

Testing has revealed that CYTOSORB beads remove various molecules relevant to inflammation in sepsis, including: TNF, IL-6, IL-10, HMGB-1, IL-8, IL-18, MCP-1, IL-2, IL-1β and S100B. As shown in FIG. 1, CYTOSORB shows in vitro cytokine elimination. The data shown in FIG. 1 is means±SE for six pools of blood from two animals each. All time points were significantly different form time 0, $p<0.0001$. As shown in FIG. 2, CYTOSORB removes HMGB-1 in RAW 264.7 Cells stimulated with LPS in the presence or absence of polymer.

EXAMPLES

The following examples explain embodiments of the present invention in more detail. However, these examples are given for the purpose of illustration and not limitation.

Briefly, a hemoadsorption device containing CYTOSORB polymer has been tested for the treatment of systemic inflammation due to sepsis, endotoxemia and brain death. CYTOSORB successfully removes circulating inflammatory mediators in a hemoadsorption device, resulting in reduced DNA binding in the liver and improved survival time in animals.

Example 1

Treatment with CYTOSORB Beads and $NF_{-k}B$ DNA-Binding

In one set of experiments, 12 animals were studied after intravenous lipopolysaccharide (LPS) injection, six sham and six treated with CYTOSORB using a 10-g device and an aterial-venous circuit. All animals were euthanized after four hours of perfusion so that liver tissue could be obtained for determination of $NF_{-k}B$ DNA-binding. The results, shown in FIG. 3, indicate that $NF_{-k}B$ DNA-binding was significantly lower for CYTOSORB-treated animals as compared to sham-treated animals ($p=0.03$).

Example 2

Treatment with CYTOSORB Beads and Short-Term Survival

In a separate set of experiments, randomized 40 animals were randomized to receive either hemoadsorption or treatment using a sham circuit for four hours beginning immediately following a lethal LPS infusion. Following the termination of perfusion at four hours, the animals received only fluid resuscitation for the next 8 hours. All animals were sacrificed at 12 hours. Animals treated with CYTOSORB demonstrated a 21% increase in survival time ($p>0.01$). In the sham-perfusion group, 19 of 20 animals died before 12 hours, while 7 of 20 rats that received hemoperfusion with CYTOSORB were alive at 12 hours, representing an overall improvement in survival (form 5% to 35%, $p=0.02$). Circulating plasma IL-6, TNF and IL-10 levels for animals treated with CYTOSORB were also significantly lower and their concentrations were inversely correlated with survival time $p=0.003$.

Example 3

Enteral CYTOSORB Improves Survival in Septic Rats

Preliminary experiments were conducted in 22 rats using an established lethal model of sepsis, cecal ligation and puncture (CLP). Survival was measured with and without enteral CYTOSORB therapy. The results are shown in FIG. 4. Compared to controls, CYTOSORB-treated animals had significantly improved survival (36% vs. 9%), $p=0.03$. It is important to emphasize that this significant improvement in survival was obtained using only enteral administration of the CYTOSORB beads. Presumably, the presence of these beads within the lumen of gastrointestinal tract acted as a sink for deleterious mediators released into the gut via the bile and/or secreted by immunostimulated enterocytes.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of ameliorating inflammation in a patient suffering from or at risk of inflammation comprising:

administering to the patient a therapeutically effective dose of a composition comprising a sorbent, wherein the sorbent comprises both polystyrene divinyl benzene copolymer and polyvinyl pyrrolidone polymer, wherein the administration results in enteral adsorption of an inflammatory mediator.

2. The method of claim 1, wherein an inflammatory mediator is associated with sepsis, surgery, cytotoxic chemotherapy, bone marrow manipulation, major tissue injury, mesenteric hypoperfusion, gut-mucosal injury, malaria, local gastrointestinal inflammatory disease, acute lung inflammation, pancreatitis, rheumatoid arthritis, or collagen vascular diseases.

3. The method of claim 1, wherein the administration is oral or rectal.

4. The method of claim 1, wherein the administration is via feeding tube.

5. The method of claim 1, wherein the patient is human.

6. The method of claim 1, wherein the inflammation is systemic.

7. The method of claim 1, wherein the inflammation is associated with local gastro-intestinal injury or disease.

8. The method of claim 1, wherein the composition consists essentially of the sorbent.

9. The method of claim 1, wherein the sorbent is in the form of beads.

10. The method of claim 9, wherein the beads comprise polystyrene divinyl benzene copolymer with a polyvinyl pyrrolidone polymer coating.

11. The method of claim 9, wherein the beads consist essentially of polystyrene divinyl benzene copolymer and polyvinyl pyrrolidone polymer.

12. The method of claim 9, wherein the bead diameter is about 200 μm to about 800 μm.

13. The method of claim 9, wherein the beads have pores on the surface of the beads.

14. The method of claim 13, wherein the pores have a diameter of about 10 Å to about 100 Å.

15. The method of claim 13, wherein the beads comprise a distribution of pore sizes.

16. The method of claim 13, wherein the pores have a diameter of at least 10 Å.

17. The method of claim 9, wherein the beads have an internal surface area of about 700 m² per gram to about 1000 m² per gram of beads.

18. The method of claim 9, wherein the beads adsorb cytokines.

19. The method of claim 9, wherein the beads adsorb one or more molecules selected from the group consisting of tumor necrosis factor (TNF), interleukin (IL)-6, IL-10, high mobility group protein B (HMGB)-1, IL-8, IL-18, monocyte chemotactic protein (MCP)-1, IL-2, IL-1β, and S100B.

20. The method of claim 9, wherein composition is in the form of a pill comprising the beads and a pharmaceutically acceptable excipient.

21. The method of claim 9, wherein the beads are administered in the form of a slurry, gel, or powder comprising the beads.

22. The method of claim 9, wherein the beads have a diameter of at least 200 μm.

23. The method of claim 9, wherein the beads have an internal surface area of at least 700 m² per gram of beads.

24. A method of treating a patient suffering from an inflammatory response comprising:

enterally administering to the patient a therapeutically effective dose of a composition consisting essentially of polystyrene divinyl benzene copolymer and a polyvinyl pyrrolidone polymer.

25. The method of claim 24, wherein the composition consisting essentially of the polystyrene divinyl benzene copolymer and polyvinyl pyrrolidone polymer is in the form of beads.

26. The method of claim 25, wherein the beads consist essentially of polystyrene divinyl benzene copolymer with a polyvinyl pyrrolidone polymer coating.

27. The method of claim 24, wherein the composition is administered orally, rectally, or via a feeding tube.

28. The method of claim 24, wherein the patient is human.

29. The method of claim 24, wherein the inflammatory response is systemic.

30. The method of claim 24, wherein the inflammatory response is associated with local gastro-intestinal injury or disease.

31. A method of reducing inflammation in a patient suffering from or at risk of same, comprising:

enterally administering to the patient a therapeutically effective dose of a composition comprising beads of a sorbent that adsorbs a mediator of inflammation, wherein the sorbent comprises both polystyrene divinyl benzene copolymer and polyvinyl pyrrolidone polymer.

32. The method of claim 31, wherein the beads comprise polystyrene divinyl benzene copolymer with a polyvinyl pyrrolidone polymer coating.

33. The method of claim 31, wherein the patient is human.

34. The method of claim 31, wherein the inflammation is systemic.

35. The method of claim 31, wherein the inflammation is associated with local gastro-intestinal injury or disease.

36. The method of claim 31, wherein the composition consists essentially of the beads of a sorbent.

37. An orally-admissible pharmaceutical dosage form comprising, as active principal, beads comprising both polystyrene divinyl benzene copolymer and polyvinyl pyrrolidone polymer.

38. The dosage form of claim 37, comprising one or more pharmaceutically acceptable excipients.

39. The dosage form of claim 37, which is in the form of a capsule.

40. The dosage form of claim 37, in the form of a pill, slurry, gel, or powder.

41. The dosage form of claim 37, wherein the beads comprise polystyrene divinyl benzene copolymer coated with a polyvinyl pyrrolidone polymer.

42. The dosage form of claim 37, wherein the beads consist essentially of polystyrene divinyl benzene copolymer and polyvinyl pyrrolidone polymer.

43. The dosage form of claim 37, wherein the bead diameter is at least 200 μm.

44. The dosage form of claim 37, wherein the beads have pores on the surface of the beads.

45. The dosage form of claim 44, wherein said pores have a diameter of at least 10 Å.

46. The dosage form of claim 37, wherein the beads comprise a distribution of pore sizes.

47. The dosage form of claim 37, wherein the beads have an internal surface area of at least 700 m² per gram of beads.

* * * * *